United States Patent [19]
Auge et al.

[11] 4,003,924
[45] Jan. 18, 1977

[54] PROCESS FOR PREPARING 1-AMINO ANTHRAQUINONE

[75] Inventors: Wolfgang Auge, Odenthal-Hahnenberg; Karl-Werner Thiem, Cologne; Rütger Neeff, Leverkusen; Paul Losacker, Leichlingen; Rudolf Braden, Odenthal, all of Germany

[73] Assignee: Bayer Aktiengesellschaft, Leverkusen, Germany

[22] Filed: Feb. 3, 1975

[21] Appl. No.: 546,833

[30] Foreign Application Priority Data

Mar. 5, 1974  Germany ................... 2410310

[52] U.S. Cl. ................... 260/382; 260/378
[51] Int. Cl.² ................... C07C 97/24
[58] Field of Search ............ 260/382, 378, 581
[56] References Cited

UNITED STATES PATENTS 1,792,348  2/1931  Ackermann et al. ............ 260/378

FOREIGN PATENTS OR APPLICATIONS 6,526       1878   Germany
2,211,411   9/1972 Germany

OTHER PUBLICATIONS

Barnett, Antracene and Anthraquinone, D. Von Nostrand Co., New York, N. Y. 1921, pp. 195-201.
Lubs, The Chemistry of Synthetic Dyes & Pigments, A.C.S. Monograph, 1955, p. 361.

Primary Examiner—Arthur P. Demers
Attorney, Agent, or Firm—Burgess, Dinklage & Sprung

[57] ABSTRACT

1-Amino anthraquinone is prepared by reacting 1-nitro-anthraquinone with ammonia in water and/or an organic solvent and thereafter treating the 1-aminoanthraquinone imine formed with water thereby converting said imine into 1-amino anthraquinone.

13 Claims, No Drawings

PROCESS FOR PREPARING 1-AMINO ANTHRAQUINONE

BACKGROUND

This invention relates to a process for preparing 1-amino anthraquinone from the reaction of 1-nitro-anthraquinone with ammonia in water and/or an organic solvent followed by treatment of the 1-amino anthraquinone imine formed with water to convert same into 1-amino anthraquinone.

Processes for the preparation of 1-amino-anthraquinone by reacting 1-nitro-anthraquinone with ammonia in water (R. Oda, J. Soc. Chem. Ind., Japan, 43. Suppl.,binding 386 (1940)) and acid amides (German Offenlegungsschrift No. 2,211,411) are known.

The yields of 1-amino-anthraquinone obtained by these processes, however, are not substantially higher than 94% and 80% respectively. It is found that when the reaction is carried out in these, as well as in other, organic solvents, e.g. in substituted or unsubstituted aromatic or aliphatic solvents, nitriles, esters, sulphones, ethers and alcohols, the 1-amino-anthraquinone undergoes a secondary reaction to form substantial quantities of 1-amino-anthraquinone monoimine, depending on the reaction conditions.

The formation of 1-amino-anthraquinone imine is particularly pronounced if an excess of ammonia is used for the amination reaction. Such ammonia excess is, however, necessary in order to obtain complete conversion within economical reaction times. The 1-amino-anthraquinone imine formed in this reaction (in the most favourable case 1 to 10%, based on the quantity of nitro-anthraquinone introduced) reduces the yield of 1-amino-anthraquinone.

SUMMARY

It has now surprisingly been found that 1-amino-anthraquinone imine may easily be converted into 1-amino-anthraquinone, the purity of 1-amino-anthraquinone and reaction yield being thereby considerably increased.

The process according to the invention is characterised in that after the reaction of 1-nitro-anthraquinone with ammonia in water and/or organic solvents, such as substituted or unsubstituted aromatic or aliphatic solvents, cycloaliphatic solvents, nitriles, esters, sulphones, tertiary amines, acid-amines, ethers, alcohols, etc., the 1-amino-anthraquinone imine formed in the reaction is converted into 1-amino-anthraquinone by treating the reaction product with water in the presence of an acid catalyst or water without an acid catalyst at a temperature of above 100° C, preferably from 150° C to 230° C.

DESCRIPTION

Conversion of 1-amino-anthraquinone imine into 1-amino-anthraquinone may be carried out, for example, by isolating the product of the reaction of 1-nitro-anthraquinone with ammonia from the reaction mixture, e.g. by filtration or removal of the solvent by distillation, and reacting the resulting mixture of 1-amino-anthraquinone (e.g. 95%, by weight) and 1-amino-anthraquinone imine (e.g. 5%, by weight) with water in organic solvents e.g. in ethers, aliphatic, cycloaliphatic or aromatic solvents, nitriles, sulphones, acid amides, tertiary amines, alcohols or esters, or by carrying this reaction out directly in water.

The reaction is accelerated by acid catalysts, e.g. by the catalytic action of acids, such as hydrochloric acid, sulphuric acid, phosphoric acid, boric acid, silicic acid, carbonic acid, acetic acid, formic acid and other inorganic or organic acids, in particular also Lewis acids, or acid ion exchangers or oxides, e.g. acid aluminium oxide, silicon oxide or carbon dioxide. With the aid of such catalysts, the reaction may already be carried out at temperatures of about 0° C and above and is preferably carried out at or above room temperature. The reaction may, for example, also be carried out directly in aqueous mineral acids.

If the reaction is carried out in solvents or in water without acid catalysis, temperatures above 100° C should be employed, in particular temperatures above 150° C, because the reaction velocity increases with rising temperature.

If the reaction is carried out in organic solvents, the reaction velocity depends also on the water content of the solvent. The water content is suitably kept between 1 and 40%, by weight, in particular 2 to 10%, by weight (based on the solvents or diluents).

Thus, for example, to react a given quantity of 1-amino-anthraquinone imine at 190° c, the time required is 60 minutes if the water content in the organic solvent (e.g. o-xylene) is 2%, by weight, and 20 minutes if the water content is 9%, by weight.

For a given water content (e.g. 2%, by weight), the reaction is completed after 60 minutes at 190° C and after 20 minutes at 210° C.

It follows that as the concentration of water in the reaction mixture decreases, the temperature must be increased to obtain the same conversion times.

According to a particularly advantageous embodiment of the process according to the invention, conversion of 1-amino-anthraquinone imine into 1-amino-anthraquinone may be carried out by substantially or completely removing the excess ammonia from the reaction medium used in the amination of 1-nitro-anthraquinone with ammonia after the reaction has been completed and then treating the remainng mixture with water, optionally with the aid of acid catalysts, as described above. Another preferred embodiment of the process involves, after partial or complete removal of the excess ammonia, carrying out the reaction in the remaining mixture at elevated temperatures with the aid of the water produced by the amination reaction.

Whereas the reaction is accelerated by acid catalysis, e.g. in the presence of the above-mentioned acids, ion exchangers or inorganic oxides, the reaction velocity decreases with increasing quantities of ammonia. Thus, for example, to convert equal 1-amino-anthraquinone imine contents in the reaction product (~5%) at 190° C and a water content of 9%, by weight, the reaction time required is 140, 80 and 25 minutes, respectively, when the molar ratio of residual ammonia to 1-amino-anthraquinone plus 1-amino-anthraquinone imine is 3.5, 1.0 and 0, respectively. With increasing ammonia content, the saponification reaction finally comes to a stand-still and the reverse reaction of formation of 1-amino-anthraquinone imine from 1-amino-anthraquinone sets in.

By "molar ratio" is meant herein the ratio of ammonia to 1-nitro-anthraquinone introduced into the reaction or to the resulting 1-amino-anthraquinone and 1-amino-anthraquinone imine.

Products which contain more than 50%, by weight, of 1-amino-anthraquinone imine may thus be obtained by employing a high molar ratio of ammonia to 1-nitro-anthraquinone or 1-amino-anthraquinone (e.g. above 30) and high temperatures (e.g. 170° C) and pressures (e.g. 100 bar) for long reaction times, preferably in the presence of water. This reaction is advantageously carried out directly in ammonia but may also be carried out quite satisfactorily in organic solvents (e.g. nitriles, aromatic solvents, aliphatic solvents, alcohols, ethers) or water.

The process according to the invention of conversion of 1-amino-anthraquinone imine into 1-amino-anthraquinone may be carried out either continuously or discontinuously, optionally under pressure.

1-amino-anthraquinone, an important dye-making intermediate, is obtained with a higher degree of purity and in higher yields by the process according to the invention than by processes hitherto known for producing 1-amino-anthraquinone by reacting ammonia with 1-nitro-anthraquinone.

The degrees referred to are degrees centigrade.

EXAMPLE 1

German Offenlegungsschrift No. 2,211,411, Example 1

26.3 g of 1-nitro-anthraquinone (96%) is suspended in 110 g of formamide. If ammonia gas is introduced at 155° C, no more starting material may be detected by thin layer chromatography after 4 hours. After complete removal of the solvent by distillation under vacuum, 22.5 g of an 80% 1-amino-anthraquinone (80% of the theoretical yield) which contains 4%, by weight of 1-amino-anthraquinone imine are obtained.

EXAMPLE 2

The product (22.5 g) obtained according to Example 1 is stirred in 150 ml of water under pressure at 190° C for 1 hour. After the pressure has been released, the water is removed by vacuum distillation. Yield: 22 g of an 84% 1-amino-anthraquinone (84% of the theoretical yield, based on the quantity of 1-nitro-anthraquinone introduced into the reaction) (1-amino-anthraquinone imine less than 0.3%, by weight).

If the reaction is carried out, e.g., at 110° C for about 10 hours, 22 g of an 83% 1-amino-anthraquinone (1-amino-anthraquinone imine approximately 1% by weight) are obtained.

EXAMPLE 3

According to R. Oda, J. Soc. Chem. Ind. Japan, 43, Suppl. binding 386 (1940).

256 g of a 99% 1-nitro-anthraquinone are reacted in 2500 g of 35% aqueous ammonia solution at 190°–200° C for 4 hours in an autoclave. After release of pressure, the reaction product is isolated by removal of the water by distillation under vacuum and dried. Yield: 226 g of a 90% 1-amino-anthraquinone (91% of the theoretical yield) which contains 5by weight, of 1-amino-anthraquinone imine.

EXAMPLE 4

The product (226 g) obtained according to Example 3 is reacted with water and worked-up as described in Example 2. Yield: 226 g of a 95% 1-amino-anthraquinone (96% of the theoretical yield based on 1-nitro-anthraquinone) less than 0.3% by weight, of 1-amino-anthraquinone imine).

EXAMPLE 5

22.6 g of the product obtained according to Example 3 are stirred in 200 ml of 20% hydrochloric acid at room temperature, diluted with 1 liter of water and suction filtered.

After the precipitate has been washed, neutralised and dried, 21.6 g of a 98% 1-amino-anthraquinone are obtained (95% of the theoretical yield based on 1-nitro-anthraquinone) (1-amino-anthraquinone imine less than 0.1% by weight). 1-amino-anthraquinone is obtained at a similar degree of purity and in similar yields when dilute sulphuric acid or phosphoric acid is used instead of hydrochloric acid.

EXAMPLE 6

In a continuous process, 256 g per hour of a 99% 1-nitro-anthraquinone in 2 liters per hour of o-xylene are reacted with 15 mols per hour of ammonia at 170° C and 100 bar in a reaction tube in which the reactants, have a residence time of 40 minutes.

The pressure is released and the reaction product is isolated by removal of the solvent and excess ammonia by distillation under vacuum. Yield per hour: 226 g of a 92% 1-amino-anthraquinone (93% of the theoretical yield) which contains 5%, by weight of 1-amino-anthraquinone imine.

Similar degrees of purity, 1-amino-anthraquinone yields and 1-amino-anthraquinone imine contents are obtained when the reaction is carried out in acetonitrile, propionitrile, dioxane, tetrahydrofuran, glycol dimethyl ether, n-pentane, glycol or cyclohexane instead of o-xylene.

EXAMPLE 7

The reaction mixture obtained immediately after the reaction in o-xylene according to Example 6 is at 170° C continuously depressurized to 20 bar, into a column, the ammonia being completely removed at the top of the column while the water produced by the reaction remains in the solution removed from the sump. This is reacted for 30 minutes in a reaction tube at 210°/20 bar. After cooling, release of pressure and removal of water and o-xylene by distillation the product is dried. Yield: 225 g per hour of a 98% 1-amino-anthraquinone (99% of the theoretical yield, based on 1-nitro-anthraquinone) (1-amino-anthraquinone imine less than 0.3%, by weight).

Similar yields and purities are also obtained when, for examples, 35 ml per hour of water (corresponding to 2%, by weight, based on the solvent) or 176 ml per hour of water (equals 10%, by weight) or 700 ml of water (equals 40%, by weight) are added to the solution removed as sump or if the reaction is carried out at 190° (in about 60 minutes at 2%, by weight, of water in about 20 minutes at 10%, by weight of water) or if the reaction is carried out in the presence of carbon dioxide (20 bar). This reaction may also be carried out discontinuously.

EXAMPLE 8

The reaction mixture which is obtained immediately after the reaction in o-xylene according to Example 6 is freed from pressure at 170° in a column from which the ammonia is not completely removed at the top so that 3.5 mols of ammonia are left in the sump solution to 1 mol of 1-amino-anthraquinone and 1-amino-anthraquinone imine. 176 ml per hour of water ( = 10% by weight, based on the solvent) are added to the sump solution and reacted for 3 hours at 190°/20 bar. The product is worked-up as described in Example 7. Yield: 225 g per hour of a 97% 1-amino-anthraquinone (98% of the theoretical yield, based on 1-nitro-anthraquinone) (1-amino-anthraquinone imine less than 0.3% by weight).

EXAMPLE 9

The reaction mixture obtained in acetonitrile according to Example 6 is continuously freed from pressure in a column according to Example 7, completely freed from ammonia diluted with water to a water content of 10% by weight, based on the solvent, and pumped through a reaction tube at a rate which provides a residence time of 1 hour at 190°. After removal of nitrile and water by distillation, the product is dried. Yield: 225 g per hour of a 97% 1-amino-anthraquinone (1-amino-anthraquinone imine less than 0.1% by weight).

Similar purities and yields are obtained when the process is carried out in dioxane or cyclohexane, optionally also continuously, instead of in acetonitrile.

EXAMPLE 10

Preparation of 1-amino-anthraquinone imine:

258 g 1-nitro-anthraquinone 98% are treated with 1033 g of ammonia at 100°/35 bar for 10 hours in 2.6 liters of acetonitrile containing 2%, by weight, of water.

The residue (225 g) obtained after cooling, release of pressure and removal of solvent by distillation contains 50%, by weight, of 1-amino-anthraquinone imine (49% by weight of 1-amino-anthraquinone according to gas-chromatic analysis). 1-amino-anthraquinone imine is separated chromatographically (petroleum hydrocarbons/tetrahydrofuran) on silica gel. Determination of the overall formula by high resolution mass spectrometry gave the result: 222.079 ME = $C_{14}H_{10}N_2O$ (theoretical 222.079).

The structure of 1-amino-anthraquinone imine is confirmed by $C^{13}$ nuclear resonance measurements (DMF–$D_7$) (quinone imine group $\delta$ = 157.06 ppm; C—$NH_2\delta$ = 153.01 ppm) and by conversion of the 1-amino-anthraquinone imine into 1-amino-anthraquinone by treatment with sulphuric acid (80%) and quantitative analysis of the ammonia liberated.

What is claimed is:

1. Process for preparing 1-amino-anthraquinone which comprises treating a reaction mixture containing 1-amino-anthraquinone imine, after substantially or completely removing ammonia therefrom, with water thereby converting said 1-amino-anthraquinone imine into 1-amino-anthraquinone.
2. Process of claim 1 wherein the 1-amino-anthraquinone imine is treated with water in the presence of an acid catalyst at a temperature in excess of 0° C.
3. Process of claim 2 wherein the temperature is in excess of 100° C.
4. Process of claim 3 wherein the temperature is from 150° C to 230° C.
5. Process of claim 1 wherein the treatment with water is carried out in the presence of a solvent selected from the group of ethers, aliphatic or cycloaliphatic compounds, aromatic compounds, nitriles, sulphones, tertiary amines, acid amides, alcohols and water.
6. Process of claim 1 wherein the said 1-amino-anthraquinone imine is one formed by reacting 1-nitro-anthraquinone with ammonia in water and/or an organic solvent and the treatment with water of said 1-amino-anthraquinone imine is carried out directly in the reaction mixture obtained from the amination of 1-nitroanthraquinone after substantial or complete removal of the excess ammonia and optionally after the addition of water.
7. Process of claim 2 wherein the acid catalyst is selected from the group of organic or inorganic acids, Lewis acids, acid ion exchangers and acidic oxides.
8. Process of claim 1 wherein the treatment with water is carried out in an organic solvent containing from 1 to 40% by weight based on the organic solvent, of water.
9. Process of claim 8 wherein the water content is from 2 to 10% by weight.
10. Process of claim 6 wherein any excess ammonia employed for the reaction of 1-nitro-anthraquinone is at least partially removed from the reaction mixture prior to the treatment of said 1-amino-anthraquinone imine with water.
11. Process of claim 6 wherein water used for treating the crude product is produced by the amination reaction.
12. Process of claim 11 wherein the treatment with water is carried out at a temperature in excess of 150° C.
13. Process of claim 1 carried out continuously.

* * * * *